United States Patent
Cao et al.

(10) Patent No.: US 10,984,024 B2
(45) Date of Patent: *Apr. 20, 2021

(54) AUTOMATIC PROCESSING OF AMBIGUOUSLY LABELED DATA

(71) Applicant: International Business Machines Corporation, Armonk, NY (US)

(72) Inventors: Yu Cao, Union City, CA (US); Yufan Guo, San Jose, CA (US); Tanveer F. Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 129 days.

This patent is subject to a terminal disclaimer.

(21) Appl. No.: 16/188,691

(22) Filed: Nov. 13, 2018

(65) Prior Publication Data

US 2019/0370387 A1 Dec. 5, 2019

Related U.S. Application Data

(63) Continuation of application No. 15/992,622, filed on May 30, 2018.

(51) Int. Cl.
*G06F 16/28* (2019.01)
*G06N 5/02* (2006.01)
(Continued)

(52) U.S. Cl.
CPC ............ *G06F 16/285* (2019.01); *G06F 16/51* (2019.01); *G06N 3/04* (2013.01); *G06N 5/02* (2013.01); *G16H 30/20* (2018.01)

(58) Field of Classification Search
CPC ..... G16H 50/20; G06F 16/285; G06F 16/906; G06N 20/00; G06N 3/08
(Continued)

(56) References Cited

U.S. PATENT DOCUMENTS

| 1,055,319 A | * | 3/1913 | Chenoweth | D05B 37/08 |
| | | | | 112/122.3 |
| 6,907,436 B2 | | 6/2005 | Ye et al. | |
| 8,200,487 B2 | | 6/2012 | Peters et al. | |
| 8,332,221 B2 | | 12/2012 | Peters et al. | |

(Continued)

OTHER PUBLICATIONS

Zeng, Zinan et al., "Learning by Associating Ambiguously Labeled Images", IEEE, CVPR '13 Proceedings of the 2013 IEEE Conference on Computer Vision and Pattern Recognition, Jun. 23-28, 2013, 8 pages.

(Continued)

*Primary Examiner* — Hung T Vy
(74) *Attorney, Agent, or Firm* — Francis Lammes; William J. Stock; Stephen J. Walder, Jr.

(57) ABSTRACT

A mechanism is provided that implements a cognitive data processing system for automatically processing ambiguously labeled data associated with a medical image. The cognitive data processing system receives an ambiguously labeled set of training data in which the ambiguously labeled set of training data comprises portions of data and associated labels, and wherein at least one portion of data in the ambiguously labeled set of training data has a plurality of different labels that together render the portion of data ambiguously labeled. The cognitive data processing system configures an implementation of a model that comprises a loss term, a maximizing term, and a sparsity term. The cognitive data processing system processes the ambiguously labeled set of training data based on the model to identifying a mapping that minimizes a loss function and thereby train the cognitive data processing system.

20 Claims, 3 Drawing Sheets

(51) Int. Cl.
*G06N 3/04* (2006.01)
*G16H 30/20* (2018.01)
*G06F 16/51* (2019.01)

(58) Field of Classification Search
USPC .......................................................... 707/738
See application file for complete search history.

(56) References Cited

U.S. PATENT DOCUMENTS

| | | | |
|---|---|---|---|
| 8,554,555 | B2 | 10/2013 | Gruhn et al. |
| 8,688,448 | B2 | 4/2014 | Peters et al. |
| 9,128,906 | B2 | 9/2015 | Peters et al. |
| 9,477,906 | B2 | 10/2016 | Röder et al. |
| 10,553,316 | B1 * | 2/2020 | Neumann ............... G16H 50/00 |
| 2009/0228299 | A1 | 9/2009 | Kangarloo et al. |
| 2012/0207359 | A1 | 8/2012 | Konukoglu et al. |
| 2015/0173701 | A1 | 6/2015 | Major et al. |
| 2017/0132512 | A1 | 5/2017 | Ioffe et al. |
| 2019/0034764 | A1 * | 1/2019 | Oh ......................... G06N 7/005 |

OTHER PUBLICATIONS

List of IBM Patents or Patent Applications Treated as Related, Nov. 1, 2018, 2 pages.

Chen, Yi-Chen et al., "Dictionary Learning from Ambiguously Labeled Data", IEEE, CVPR '13 Proceedings of the 2013 IEEE Conference on Computer Vision and Pattern Recognition, Jun. 23-28, 2013, 8 pages.

Cour, Timothee et al., "Learning from Partial Labels", Journal of Machine Learning Research, vol. 12, May 2011, pp. 1501-1536.

High, Rob, "The Era of Cognitive Systems: An Inside Look at IBM Watson and How it Works", IBM Corporation, Redbooks, Dec. 12, 2012, 16 pages.

Hüllermeier, Eyke et al., "Learning from Ambiguously Labeled Examples", Internal Symposium on Intelligent Data Analysis (IDA) 2005: Advances in Intelligent Data Analysis VI, Sep. 8-10, 2005, 33 pages.

Nguyen, Nam et al., "Classification with Partial Labels", ACM, KDD'08, Las Vegas, Nevada, Aug. 24-27, 2008, 9 pages.

* cited by examiner

AUTOMATIC PROCESSING OF AMBIGUOUSLY LABELED DATA

BACKGROUND

The present application relates generally to an improved data processing apparatus and method and more specifically to mechanisms for automatic processing of ambiguously labeled data.

Medical imaging is the technique and process of creating visual representations of the interior of a human body for clinical analysis and medical intervention, as well as visual representation of the function of some organs or tissues (physiology). Medical imaging seeks to reveal internal structures hidden by the skin and bones, as well as to diagnose and treat disease. Utilizing the medical images from a plurality of patients, a medical image database may be established of normal anatomy and physiology for use in identifying medical images of other patients that have possible abnormalities.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions that are executed by the at least one processor to cause the at least one processor to be configured to implement cognitive data processing system for automatically processing ambiguously labeled data associated with a medical image. The method comprises receiving, by the cognitive data processing system, an ambiguously labeled set of training data in which the ambiguously labeled set of training data comprises portions of data and associated labels, and wherein at least one portion of data in the ambiguously labeled set of training data has a plurality of different labels that together render the portion of data ambiguously labeled. The method further comprises configuring, by the cognitive data processing system, an implementation of a model that comprises a loss term, a maximizing term, and a sparsity term, wherein the loss term operates to evaluate candidate classes of data types in which portions of data in the ambiguously labeled set of training data may be classified, wherein the maximizing term operates to identify a single candidate class for a portion of data having ambiguous labels, and wherein the sparsity term operates to assess a number of non-zero elements for ambiguous labels. In addition, the method comprises processing, by the cognitive data processing system, the ambiguously labeled set of training data based on the model to identifying a mapping that minimizes a loss function and thereby train the cognitive data processing system.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
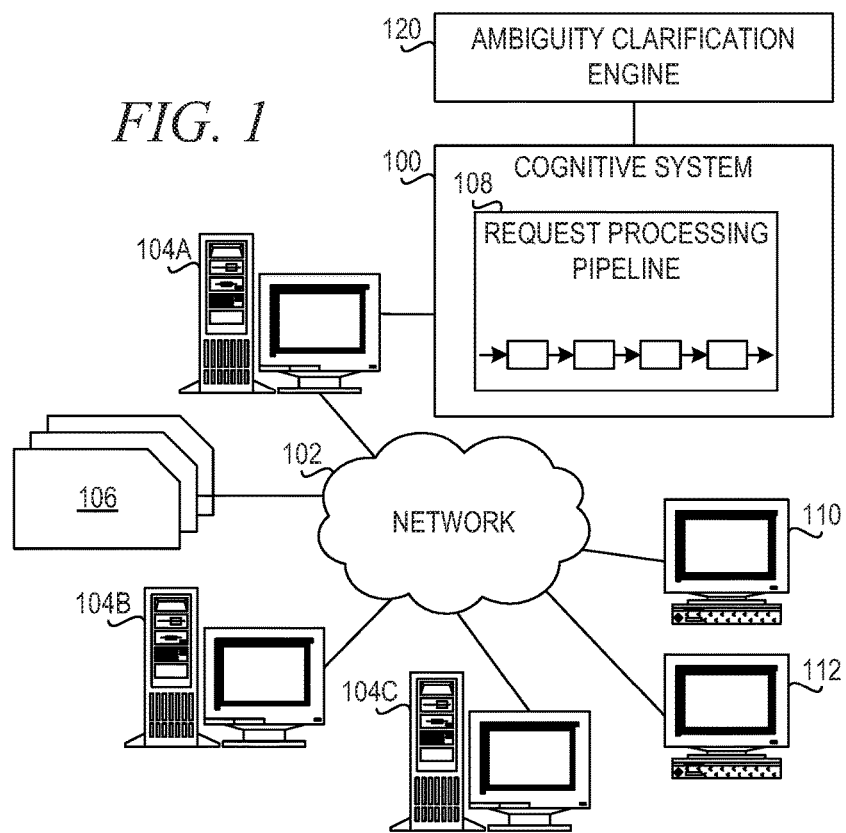
FIG. 1 depicts a schematic diagram of one illustrative embodiment of a cognitive system in a computer network.

As noted previously, medical images from a plurality of patients may be utilized to establish a medical image database of normal anatomy and physiology for use in identifying medical images of other patients that have possible abnormalities or anatomical structures. In order to train a deep-learning cognitive system to identify abnormalities or anatomical structures within a medical image, deep-learning cognitive systems automatically extract relevant features from raw medical images that differ from images of a normal anatomy and/or physiology. However, a current barrier to training such deep-learning cognitive systems is obtaining accurately labeled medical image datasets. Obtaining accurately labeled medical image datasets may be difficult in large electronic medical records (EMRs) that may show not only data entry errors but also combine findings in related reports, which may lead to ambiguities in labels that may be associated with individual medical images.

Thus, the illustrative embodiments provide mechanisms for automatically processing ambiguously labeled data associated with a medical image. That is, the illustrative embodiments utilize ambiguously labeled data sets to train deep-learning cognitive systems that are utilized to identify abnormalities or anatomical structures in medical images. Specifically, when a medical image is ambiguously labeled or not labeled at all, the mechanisms of the illustrative embodiment treat the ambiguously-labeled medical image as a definite negative example for all class labels outside a candidate class as well as a positive example for one and only one candidate class. The mechanisms utilize a novel loss function that models ambiguity by combining a traditional loss term with both a maximizing term and sparsity constraint. The resulting objective function replaces traditional classification stages in current deep-learning cognitive systems.

The present invention operates on different and novel perspectives of characteristics of ambiguous labels utilized to describe the medical image. The mechanisms of the illustrative embodiments model implicit information conveyed in a set of candidate labels with and without ambiguity where a true label comes from the candidate set even though there may be uncertainty about which label is correct and where class labels outside the candidate set are unequivocally wrong labels. The mechanisms model a novel loss function in the form of separate penalty terms. The first penalty term is modeled by a maximizing term to encourage the maximum of the probabilities for candidate labels to be close to 1 and a sparsity term that constrains the remaining probabilities for candidate labels close to 0. The second penalty term is modeled by a traditional loss term to ensure that the probability of each label outside the candidate set is close to 0.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides mechanisms for automatically processing ambiguously labeled data. Utilizing ambiguously labeled data sets, an ambiguity clarification engine trains deep-learning cognitive systems by treating an ambiguously-labeled medical image as a definite negative example for all class labels outside a candidate set as well as a positive example for one and only one of a candidate class. Then, the ambiguity clarification engine utilizes a novel loss function that models ambiguity by combining a traditional loss term with both a maximizing term and sparsity constraint, such that the resulting objective function replaces traditional classification stages in current deep-learning cognitive systems.

Figure 2:
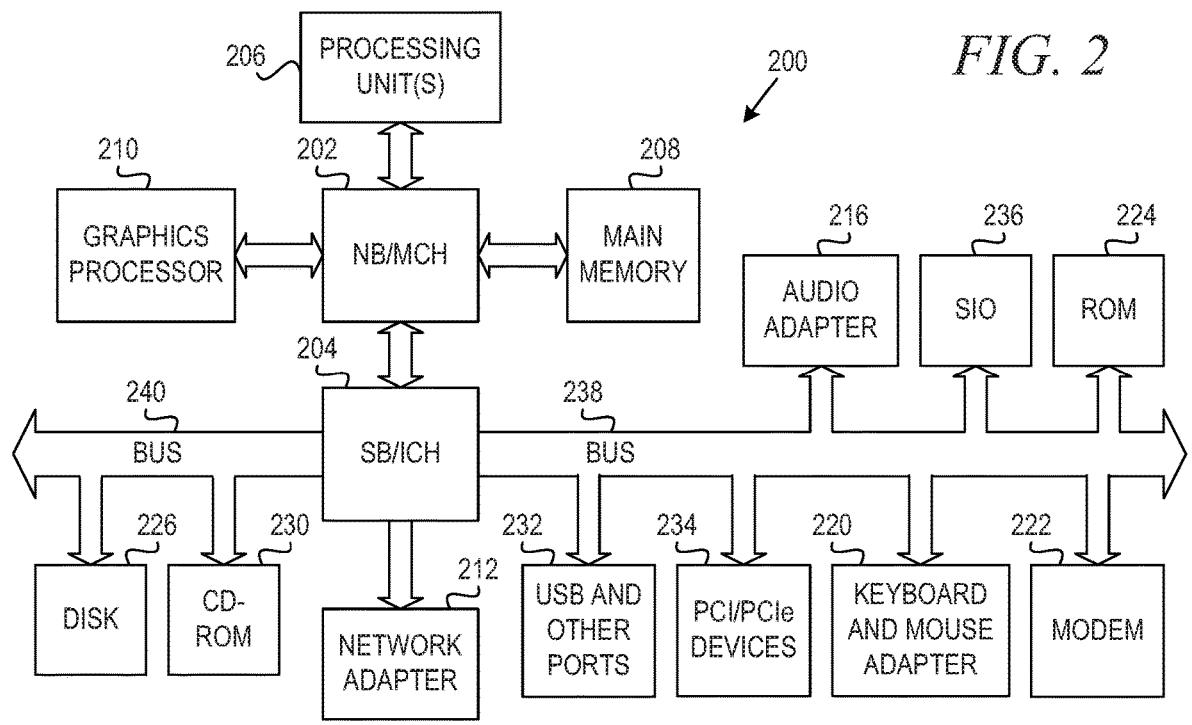
FIG. 2 is a block diagram of an example data processing system in which aspects of the illustrative embodiments are implemented.
Figure 3:
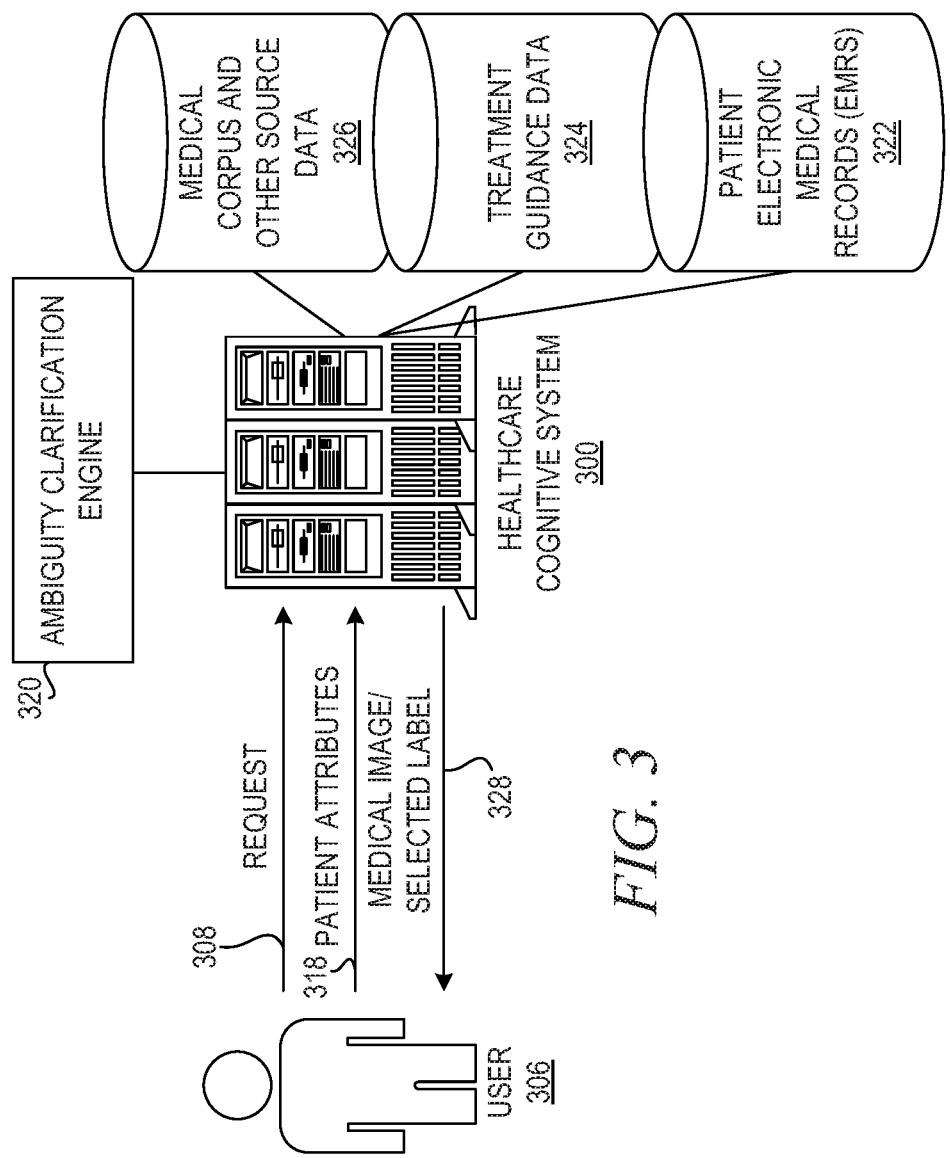
FIG. 3 is an example diagram illustrating an interaction of elements of a deep-learning cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example deep-learning cognitive system for automatically processing ambiguously labeled data, the deep-learning cognitive system implementing a request processing pipeline, request processing methodology, and request processing computer program product with which the mechanisms of the illustrative embodiments are implemented. These requests may be provided as structure or unstructured request messages, natural language questions, or any other suitable format for requesting an operation to be performed by the deep-learning cognitive system. As described in more detail hereafter, the particular application that is implemented in the deep-learning cognitive system of the present invention is an application for identifying abnormalities or anatomical structures within a medical image of a patient.

It should be appreciated that the deep-learning cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests, depending on the desired implementation. For example, in some cases, a first request processing pipeline may be trained to operate on input requests directed to a identifying an abnormality or anatomical structures within a medical image of a patient, where a first medical malady domain is associated with, for example, various types of blood diseases, while another request processing pipeline may be trained to operate on input requests directed to a identifying an abnormality or anatomical structure within a medical image of a patient in another medical malady domain associated with, for example, various types of cancers. In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have its own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The deep-learning cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As will be discussed in greater detail hereafter, the illustrative embodiments may be integrated in, augment, and extend the functionality of the request processing pipeline to include mechanisms of a deep-learning cognitive system with regard identifying key images from medical imaging studies based on image analysis and clinical knowledge protocols.

Thus, it is important to first have an understanding of how cognitive systems in a cognitive system implementing a request processing pipeline is implemented before describing how the mechanisms of the illustrative embodiments are integrated in and augment such cognitive systems and request processing pipeline mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input requests to the cognitive system 100 that are processed based on the content in the corpus or corpora of data 106. In one embodiment, the requests are formed using natural language. The cognitive system 100 parses and interprets the request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate responses while in other illustrative embodiments, the cognitive system 100 provides a single final response or a combination of a final response and ranked listing of other candidate responses.

The cognitive system 100 implements the pipeline 108 which comprises a plurality of stages for processing an input request based on information obtained from the corpus or corpora of data 106. The pipeline 108 generates responses for the input question or request based on the processing of the input request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input request which it then parses to extract the major features of the request, which in turn are then used to formulate queries that are applied to the corpus or corpora of data 106. Based on the application of the queries to the corpus or corpora of data 106, a set of hypotheses, or candidate responses to the input request, are generated by looking across the corpus or corpora of data 106 for portions of the corpus or corpora of data 106 (hereafter referred to simply as the corpus 106) that have some potential for containing a valuable response to the input response. The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics medical practice management systems, personal patient care plan generation and monitoring, patient electronic medical record (EMR) evaluation for various purposes. Thus, the cognitive system 100 may be a healthcare cognitive system 100 that operates in the medical or healthcare type domains and which may process requests for such healthcare operations via the request processing pipeline 108 input as either structured or unstructured requests, natural language input, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing an ambiguity clarification engine 120, which is described in further detail below.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsofts Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a deep-learning cognitive system in accordance with one illustrative embodiment. The example diagram of FIG. 3 depicts an implementation of a deep-learning cognitive system 300 that is configured to identify abnormalities or anatomical structures within a medical image of patient. However, it should be appreciated that this is only an example implementation and other healthcare operations may be implemented in other embodiments of the deep-learning cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the deep-learning cognitive system 300 will be electronic via a user computing device (not shown), such as a client computing device 110 or 112 in FIG. 1, communicating with the deep-learning cognitive system 300 via one or more data communication links and potentially one or more data networks.

As shown in FIG. 3, in accordance with one illustrative embodiment, the user 306 submits a request 308 to the deep-learning cognitive system 300, such as via a user interface on a client computing device that is configured to allow users to submit requests to the deep-learning cognitive system 300 in a format that the deep-learning cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, symptoms, and other pertinent information obtained from responses to questions or information obtained from medical equipment used to monitor or gather data about the condition of the patient. Any information about the patient that may be relevant to a cognitive evaluation of the patient by the deep-learning cognitive system 300 may be included in the request 308 and/or patient attributes 318.

The deep-learning cognitive system 300 provides a cognitive system that is specifically configured to perform an implementation specific healthcare oriented cognitive operation. In the depicted example, this healthcare oriented cognitive operation is directed to identifying ambiguities within a medical image of the patient in order to assist the user 306 in treating the patient based on their reported symptoms and other information gathered about the patient. The deep-learning cognitive system 300 operates on the request 308 and patient attributes 318 utilizing information gathered from the medical corpus and other source data 326, treatment guidance data 324, and the patient EMRs 322 associated with the patient to identify abnormalities or anatomical structures within a medical image of the patient.

Thus, in accordance with the illustrative embodiments herein, deep-learning cognitive system 300 is augmented to include ambiguity clarification engine 320 that models implicit information conveyed in a set of candidate labels with and without ambiguity such that:

1. A true label comes from a candidate set even though there is uncertainty about which label is correct, and
2. Class labels outside the candidate set are unequivocally wrong labels.

Thus, ambiguity clarification engine 320 models the implicit information in separate penalty terms. Ambiguity clarification engine 320 models the first penalty term is modeled by a maximizing term to encourage the maximum of the probabilities for candidate labels to be close to 1 along with a sparsity term that constrains the remaining probabilities for candidate labels close to 0. Ambiguity clarification engine 320 models the second penalty term by a traditional $l_2$ loss to ensure that the probability of each label outside the candidate set is close to 0.

Accordingly, ambiguity clarification engine 320 utilizes a collection of labeled data, such as, for example:

$$\{(X^{(m)}, Y^{(m)})\}_{m=1}^{M}$$

where M is the number of training data, $X^{(m)} \in R^N$ is the m-th data represented with an N-dimensional feature vector, R is a real number, $Y^{(m)} \in \{0,1\}^Q$ is the indicator vector for the m-th data with a 1 in each candidate label position, and Q being the total number of classes, such that:

$$Y_q^{(m)} = \begin{cases} 1, & \text{if } q \in C^{(m)}, \\ 0, & \text{otherwise} \end{cases}$$

where $C^{(m)}$ is the set of labels assigned to $X^{(m)}$ to generate a loss function:

$$L(\psi, X, Y, \sigma) = \frac{1}{2M} \sum_{m=1}^{M} \|(\psi(X^{(m)}) - Y^{(m)}) \odot I^{(m)}\|_2^2 + \quad (1)$$

$$\frac{1}{2M} \sum_{m=1}^{M} (1 - \|\psi(X^{(m)}) \odot \neg I^{(m)}\|_\infty)^2 + \frac{\sigma}{M} \sum_{m=1}^{M} \|\psi(X^{(m)}) \odot \neg I^{(m)}\|_0,$$

wherein $\psi: R^N \to (0,1)^Q$ is a mapping function from the feature space to the label space, and $$I^{(m)} = \begin{cases} \neg Y^{(m)}, & \text{if } \|Y^{(m)}\|_1 > 1, \\ 1, & \text{otherwise} \end{cases}$$

More specifically, the first term is a traditional l2 loss that is activated only for the labels without uncertainty by the switch function $I^{(m)}$, where each data may be treated as a definite negative example for all classes outside the ambiguous set and where each unambiguously labeled example may be treated as a definite positive example for the single candidate class.

The second term takes the maximum of the model outputs for all ambiguous labels assigned to an example (activated by $\neg I^{(m)}$) and measures how close it is to 1. The idea is to guide the model such that its output for at least one of the candidate classes is close to 1. The third term is a sparsity constraint weighted by σ for assessing the number of non-zero elements in the model outputs for ambiguous labels (again, activated by $\neg I^{(m)}$). σ is a hyperparameter (a configuration external to the machine learning model), whose value may be set by a practitioner, using heuristics, and tuned for the task at hand.

Note that minimizing the above "ambiguous" loss might lead to suboptimal solutions, where the model output for a false label from the candidate label set might be higher than the output for the true label. To avoid premature convergence, ambiguity clarification engine 320 introduces an additional penalty term that computes the expectation of loss on the candidate label set, with respect to a uniform distribution given that no prior knowledge is available about which candidate labels are more likely to be correct than others, such that:

$$\tilde{L} = L + \frac{1}{2M} \sum_{m=1}^{M} \frac{\|(\psi(X^{(m)}) - Y^{(m)}) \odot \neg I^{(m)}\|_2^2}{\|\neg I^{(m)}\|_1}. \quad (2)$$

Ambiguity clarification engine 320 then formulates the ambiguous learning problem as finding the mapping function ψ that minimizes the loss function of Equation (2), namely:

$$\psi^* = \arg\min \tilde{L}(\psi, X, Y, \sigma). \quad (3)$$

Given a testing example X and the learned mapping function ψ, ambiguity clarification engine 320 classifies X into a class where the class index is $$q^* = \arg\max \psi(X)_q. \quad (4)$$

Ambiguity clarification engine 320 then turns to optimization. The infinity norm in Equation (1) is not convex nor differentiable, thus minimizing Equation (1) is usually difficult. As an alternative, ambiguity clarification engine 320 approximates the infinity norm based on a maximizing term in the form of:

$$\Delta(X, \alpha) = \frac{\sum_{n=1}^{N} \cdot \exp(\alpha X_n)}{\sum_{n=1}^{N} \exp(\alpha X_n)}, \quad (5)$$

with $$\Delta(X, \alpha) \to \|X\|_\infty, \text{ as } \alpha \to \infty.$$

Note that Equation (5) is continuous and differentiable with derivative in the form of $$\partial \Delta(X_n, \alpha) = \frac{\exp(\alpha X_n)}{\sum_{n=1}^{N} \exp(\alpha X_n)} (1 + \alpha(X_n - \Delta(X, \alpha))).$$

With regard to the sparsity constraint, since a loss function with $l_0$-norm is not convex and hard to optimize, ambiguity clarification engine 320 uses an alternative sparsity measurement that combines $l_1$-norm and $l_2$-norm, such that:

$$\frac{\sqrt{N} - \|X\|_1 / \|X\|_2}{\sqrt{N} - 1}. \quad (6)$$

The sparseness is 1 when vector X has a single non-zero component and 0 when the absolute values of all components are equal. The computed sparseness ranges between [0, 1] and interpolates smoothly.

The above ambiguity clarification provided by ambiguity clarification engine 320 may then be used to improve the operations of deep-learning cognitive system 300. A traditional deep learning network consists of a number of layers of feature extraction accomplishing a sequence of convolutions and maxpooling operations. The final layer is usually a maximizing layer which is a generalization of the original sigmoidal layer in older neural networks. To allow such a deep learning network to train on ambiguous labels as in the illustrative embodiments, ambiguity clarification engine 320 replaces the final layer with a full neural network that learns from ambiguous labels using Equation (2) specified previously.

Ambiguity clarification engine 320 defines a target mapping function ψ in the form of neural networks with a sigmoid output layer:

$$\psi(X)=1/(1+\exp(-X)). \quad (7)$$

Note that the term "neural networks" here refers to a category of network topologies, including 1) multi-class perceptron classifier; 2) traditional neural networks with one input layer, one hidden layer, and one output layer; and 3) deep neural networks, such as convolutional neural networks. Ambiguity clarification engine 320 chooses different neural networks topologies according to data distribution, problem size, and available computing resources. Such a mapping function has several advantages:

1. The solution for the optimization problem Equation (3) may be a very complex mapping function. The function is highly likely to be a non-linear function modeled by a large number of parameters. Such complex function may be naturally approximated by neural networks, given the fact that neural networks are able to represent any kind of non-linear functions.
2. Using sigmoid function in the output layer guarantees that $$\psi(X) \in (0,1)^Q, \forall X \in R^N,$$

3. By varying the topology, such as number of layers or neurons, different networks may be obtained to cope with problems of different sizes and from different domains,
4. The optimization of neural networks is naturally applicable to large scale problems, given the existing powerful deep learning platforms such as "GPGPU+CUDA", along with efficient optimization techniques such as "mini-batch," "stochastic gradient decent (SGD)," and "fine-tune". In SGD, the true gradient of $\tilde{L}(\psi,X,Y,\sigma)$ over all training examples is approximated by a gradient at a single example or a mini-batch of examples. As the algorithm sweeps through the training set, all parameters w in j) get updated at each training example: $w=w-\eta\nabla\tilde{L}(\psi,X^{(m)},Y^{(m)},\sigma)$, where it is a learning rate (aka step size) selected by users, and $\nabla\tilde{L}$ is the gradient of $\tilde{L}$ at $(X^{(m)},Y^{(m)})$. SGD makes the computation of the loss and gradient more tractable leading to faster convergence especially when the training data is too big to fit in the memory. It also makes it easier to incorporate new training data in an online fashion enabling more efficient model parameter tuning.

Ambiguity clarification engine 320 then combines the ambiguous data with the neural network featuring a novel loss layer with good tolerance to ambiguous labels in order to train deep-learning cognitive system 300 for further identification of abnormalities or anatomical structures within medical images. That is, once ambiguity clarification engine 320 identifies a selected one label from the set of ambiguous labels for a medical image that is less ambiguous than the other labels in the set of ambiguous labels, ambiguity clarification engine 320 may associated that label as the most appropriate label for that medical image and return the medical image and the selected label 328 to user 306 in order to identify one or more abnormalities or anatomical structures within a medical image of the patient.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (F PGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 4:
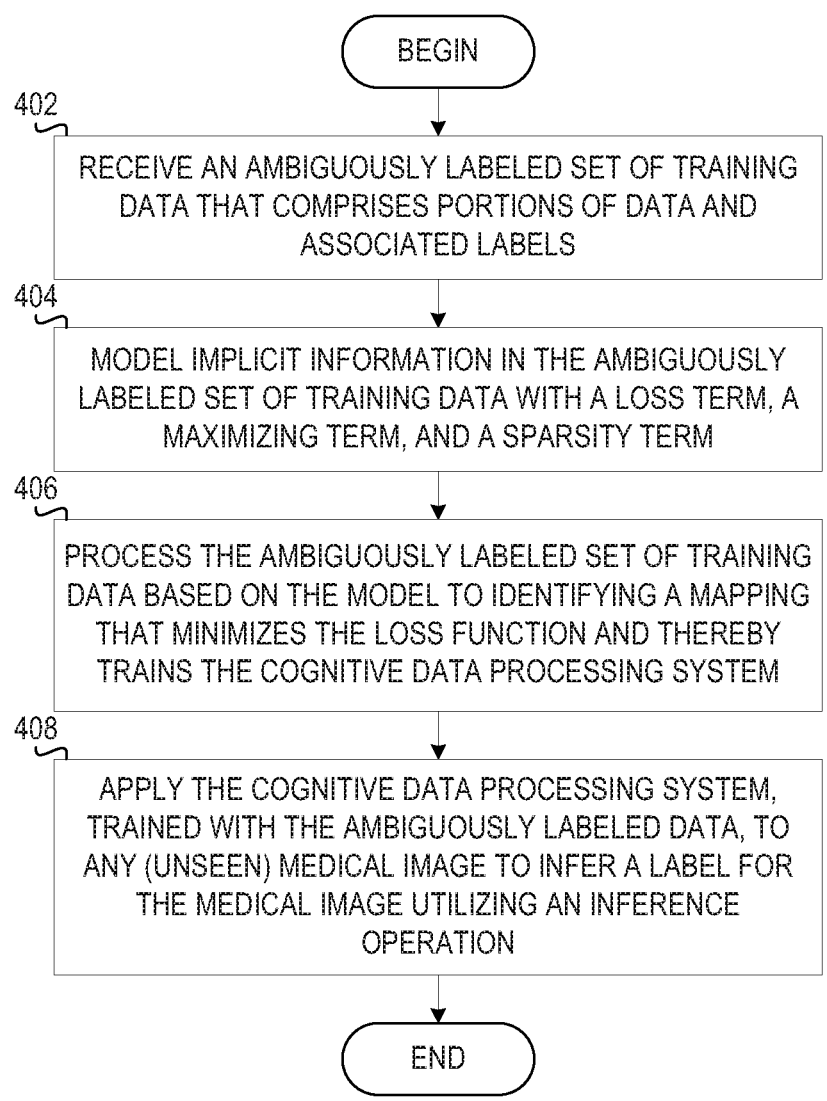
FIG. 4 depicts an exemplary flowchart of the operation performed by a deep-learning cognitive system in automatically processing ambiguously labeled data associated with a medical image in accordance with an illustrative embodiment.

FIG. 4 depicts an exemplary flowchart of the operation performed by a deep-learning cognitive system in automatically processing ambiguously labeled data associated with a medical image in accordance with an illustrative embodiment. As the operation begins, the cognitive data processing system receives an ambiguously labeled set of training data that comprises portions of data and associated labels (step 402). At least one portion of data in the ambiguously labeled set of training data has a plurality of different labels, one of which is correct, that together render the portion of data ambiguously labeled. The cognitive data processing system then models implicit information in the ambiguously labeled set of training data with a loss term, a maximizing term, and a sparsity term (step 404). The loss term operates to evaluate candidate classes of data types in which portions of data in the ambiguously labeled set of training data may be classified. The loss term treats all portions of data as negative contributors to all classes of data types outside of the ambiguous set of labels associated with the data, all portions of data having non-ambiguous labels as positive contributors to a single candidate class of data type, and all portions of data having ambiguous labels as positive contributors to one and only one class of data type inside of the ambiguous set. The maximizing term operates to identify a single candidate class for a portion of data having ambiguous labels. The sparsity term weighted by a operates to assess a number of non-zero elements for ambiguous labels. The cognitive data processing system then processes the ambiguously labeled set of training data based on the model to identify a mapping that minimizes the loss function and thereby trains the cognitive data processing system (step 406). At this point the deep "learning" process is complete. That is, the optimal mapping function $\psi$ (from an image's vector representation to its most likely label) is learned by minimizing the loss function specified in Equation (2) above. The cognitive data processing system, trained with the ambiguously labeled data, is then ready to be applied to any (unseen) medical image to infer a label for the medical image utilizing an inference operation (step 408). The application is a medical image classification operation in which one or more anatomical structures in a medical image are classified. For example, if the ambiguous labels are a set of disease/abnormality names, the trained cognitive data processing system may then be used for disease/abnormality detection on a new set of images. Additionally, once the cognitive data processing system identifies a selected one label from the set of ambiguous labels for a medical image that is less ambiguous than the other labels in the set of ambiguous labels, cognitive data processing system may associated that label as the most appropriate label for that medical image and return the medical image and the selected label to a user in order to identify one or more abnormalities or anatomical structures within a medical image of the patient. The operation terminates thereafter.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for automatically processing ambiguously labeled data associated with a medical image. That is, the illustrative embodiments utilize ambiguously labeled data sets to train deep-learning cognitive systems that are utilized to identify abnormalities or anatomical structures in medical images. Specifically, when a medical image is ambiguously labeled or not labeled at all, the mechanisms of the illustrative embodiment treat the ambiguously-labeled medical image as a definite negative example for all class labels outside a candidate class as well as a positive example for one and only one candidate class. The mechanisms utilize a novel loss function that models ambiguity by combining a traditional loss term with both a maximizing term and sparsity constraint. The resulting objective function replaces traditional classification stages in current deep-learning cognitive systems.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. 1/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions that are executed by the at least one processor to cause the at least one processor to be configured to implement a cognitive data processing system for automatically processing ambiguously labeled data associated with a medical image, the method comprising:

receiving, by the cognitive data processing system, an ambiguously labeled set of training data in which the ambiguously labeled set of training data comprises portions of data and associated labels, and wherein the associated labels comprise true labels and unequivocally wrong labels that together render the at least one portion of data ambiguously labeled;

modeling, by the cognitive data processing system, the associated labels in a set of penalty terms, wherein a first penalty term of the set of penalty terms is modeled by a maximizing term to encourage a maximum of the probabilities for a set of candidate labels in the associated labels to be close to 1 along with a sparsity term that constrains the remaining probabilities for the set of candidate labels close to 0 and wherein a second penalty term is modeled by a loss term to ensure that the probability of each associated label outside the set of candidate labels is close to 0; and training the cognitive data processing system, via a deep learning process, to identify abnormalities or anatomical structures in medical images by at least processing, by the cognitive data processing system, the ambiguously labeled set of training data based on the model to identify a mapping that minimizes a loss function for further identification of abnormalities or anatomical structures within medical images.

2. The method of claim 1, wherein the loss term treats all portions of data as negative contributors to all classes of data types outside of the set of candidate labels associated with the data, all portions of data having non-ambiguous labels as positive contributors to a single candidate class of data type, and all portions of data having ambiguous labels as positive contributors to one and only one class of data type inside of the set of candidate labels.

3. The method of claim 1, wherein a candidate label in the set of candidate labels within a predetermined distance to 1 is a true labels and wherein a candidate label in the set of candidate labels within a predetermined distance to 0 is an unequivocally wrong label.

4. The method of claim 1, further comprising:
performing, by the cognitive data processing system, an inference operation based on the trained cognitive data processing system.

5. The method of claim 4, wherein the inference operation is a medical image classification operation in which one or more anatomical structures or abnormalities in a medical image are classified.

6. The method of claim 1, wherein the sparsity term is weighted by value $\sigma$ to assess a number of non-zero elements for the set of candidate labels labels.

7. The method of claim 1, wherein the cognitive data processing system is a neural network and wherein the neural network comprises a category of network topologies, including a multi-class perceptron classifier; a traditional neural networks with one input layer, one hidden layer, and one output layer; and deep neural network.

8. A computer program product comprising a computer readable storage medium having a computer readable program stored therein, wherein the computer readable program, when executed on a cognitive data processing system, causes the cognitive data processing system to:

receive, by the cognitive data processing system, an ambiguously labeled set of training data in which the ambiguously labeled set of training data comprises portions of data and associated labels, and wherein the associated labels comprise true labels and unequivocally wrong labels that together render the at least one portion of data ambiguously labeled;

model, by the cognitive data processing system, the associated labels in a set of penalty terms, wherein a first penalty term of the set of penalty terms is modeled by a maximizing term to encourage a maximum of the probabilities for a set of candidate labels in the associated labels to be close to 1 along with a sparsity term that constrains the remaining probabilities for the set of candidate labels close to 0 and wherein a second penalty term is modeled by a loss term to ensure that the probability of each associated label outside the set of candidate labels is close to 0; and train the cognitive data processing system, via a deep learning process, to identify abnormalities or anatomical structures in medical images by at least processing, by the cognitive data processing system, the ambiguously labeled set of training data based on the model to identify a mapping that minimizes a loss function for further identification of abnormalities or anatomical structures within medical images.

9. The computer program product of claim 8, wherein the loss term treats all portions of data as negative contributors to all classes of data types outside of the set of candidate labels associated with the data, all portions of data having non-ambiguous labels as positive contributors to a single candidate class of data type, and all portions of data having ambiguous labels as positive contributors to one and only one class of data type inside of the set of candidate labels.

10. The computer program product of claim 8, wherein a candidate label in the set of candidate labels within a predetermined distance to 1 is a true labels and wherein a candidate label in the set of candidate labels within a predetermined distance to 0 is an unequivocally wrong label.

11. The computer program product of claim 8, wherein the computer readable program further causes the cognitive data processing system to:

perform, by the cognitive data processing system, an inference operation based on the trained cognitive data processing system.

12. The computer program product of claim 11, wherein the inference operation is a medical image classification operation in which one or more anatomical structures or abnormalities in a medical image are classified.

13. The computer program product of claim 8, wherein the sparsity term is weighted by value $\sigma$ to assess a number of non-zero elements for the set of candidate labels.

14. The computer program product of claim 8, wherein the cognitive data processing system is a neural network and wherein the neural network comprises a category of network topologies, including a multi-class perceptron classifier; a traditional neural networks with one input layer, one hidden layer, and one output layer; and deep neural network.

15. A cognitive data processing system comprising:
a processor, and
a memory coupled to the processor, wherein the memory comprises instructions which, when executed by the processor, cause the processor to:

receive, by the cognitive data processing system, an ambiguously labeled set of training data in which the ambiguously labeled set of training data comprises portions of data and associated labels, and wherein the associated labels comprise true labels and unequivocally wrong labels that together render the at least one portion of data ambiguously labeled;

model, by the cognitive data processing system, the associated labels in a set of penalty terms, wherein a first penalty term of the set of penalty terms is modeled by a maximizing term to encourage a maximum of the probabilities for a set of candidate labels in the associated labels to be close to 1 along with a sparsity term that constrains the remaining probabilities for the set of candidate labels close to 0 and wherein a second penalty term is modeled by a loss term to ensure that the probability of each associated label outside the set of candidate labels is close to 0; and train the cognitive data processing system, via a deep learning process, to identify abnormalities or anatomical structures in medical images by at least processing, by the cognitive data processing system, the ambiguously labeled set of training data based on the model to identify a mapping that minimizes a loss function for further identification of abnormalities or anatomical structures within medical images.

16. The cognitive data processing system of claim 15, wherein the loss term treats all portions of data as negative contributors to all classes of data types outside of the set of candidate labels associated with the data, all portions of data having non-ambiguous labels as positive contributors to a single candidate class of data type, and all portions of data having ambiguous labels as positive contributors to one and only one class of data type inside of the set of candidate labels.

17. The cognitive data processing system of claim 15, wherein a candidate label in the set of candidate labels within a predetermined distance to 1 is a true labels and wherein a candidate label in the set of candidate labels within a predetermined distance to 0 is an unequivocally wrong label.

18. The cognitive data processing system of claim 15, wherein the instructions further causes the processor to:

perform, by the cognitive data processing system, an inference operation based on the trained cognitive data processing system.

19. The cognitive data processing system of claim 18, wherein the inference operation is a medical image classification operation in which one or more anatomical structures or abnormalities in a medical image are classified.

20. The cognitive data processing system of claim 15, wherein the sparsity term is weighted by value $\sigma$ to assess a number of non-zero elements for the set of candidate labels.

* * * * *